United States Patent [19]
Kohn et al.

[11] Patent Number: 4,709,695
[45] Date of Patent: Dec. 1, 1987

[54] PROTECTIVE DEVICE

[76] Inventors: Roger Kohn, 2920 "F" St. #C-17, Bakersfield, Calif. 93301; William K. M. Shields, 20031 117th Ave. SE., Kent, Wash. 98031

[21] Appl. No.: 844,804

[22] Filed: Mar. 27, 1986

[51] Int. Cl.⁴ ............................................ A61F 13/00
[52] U.S. Cl. ................................................ 128/132 R
[58] Field of Search ............... 128/132 R, 283; 2/452, 2/436, 12, 441, 437; 351/41

[56] References Cited

U.S. PATENT DOCUMENTS

| | | | |
|---|---|---|---|
| 377,835 | 2/1888 | Lyman. | |
| 3,068,863 | 11/1959 | Bowman | 128/132 |
| 3,092,103 | 11/1959 | Mower | 128/132 |
| 3,300,786 | 1/1967 | Rusenvold et al. | 128/132 R |
| 3,339,206 | 9/1967 | Daley | 2/2 |
| 3,952,735 | 4/1976 | Wirtszhafter et al. | 128/163 |
| 4,411,263 | 10/1983 | Cook | 128/132 R |
| 4,473,370 | 9/1984 | Weiss | 604/402 |
| 4,502,476 | 3/1985 | Welt | 128/132 R |
| 4,581,877 | 4/1986 | Wilber | 128/132 R |

OTHER PUBLICATIONS

Instructional leaflet for "RMMC Photo-Mask", by Rocky Mountain Medical Corporation (Co).
Sales brochure by Keeler Instruments, Inc., p. 4 includes description of "Donaldson Natural Eyepatch".
"Argus"—Sep. 30, 1985–Kirk Morgan & William Brauer: pp. 9–10, Eye Closure Device . . . .

Primary Examiner—Gregory E. McNeill
Attorney, Agent, or Firm—Donald G. Lewis

[57] ABSTRACT

A protective device having medical applications is disclosed. The protective device includes an adhesive base and a protective covering. The adesive base adhesively attaches to the patient's skin and surrounds the area to be protected. The protective covering is coupled to the adhesive base and covers the area to be protected. The protective covering is coupled to the adhesive base by means of adhesive or Velcro (TM). The protective covering may be repeatedly decoupled and recoupled with the adhesive base without detaching the adhesive base from the patient's skin. The protective device thereby provides repeated access to the protected area without damaging the patient's skin.

11 Claims, 11 Drawing Figures

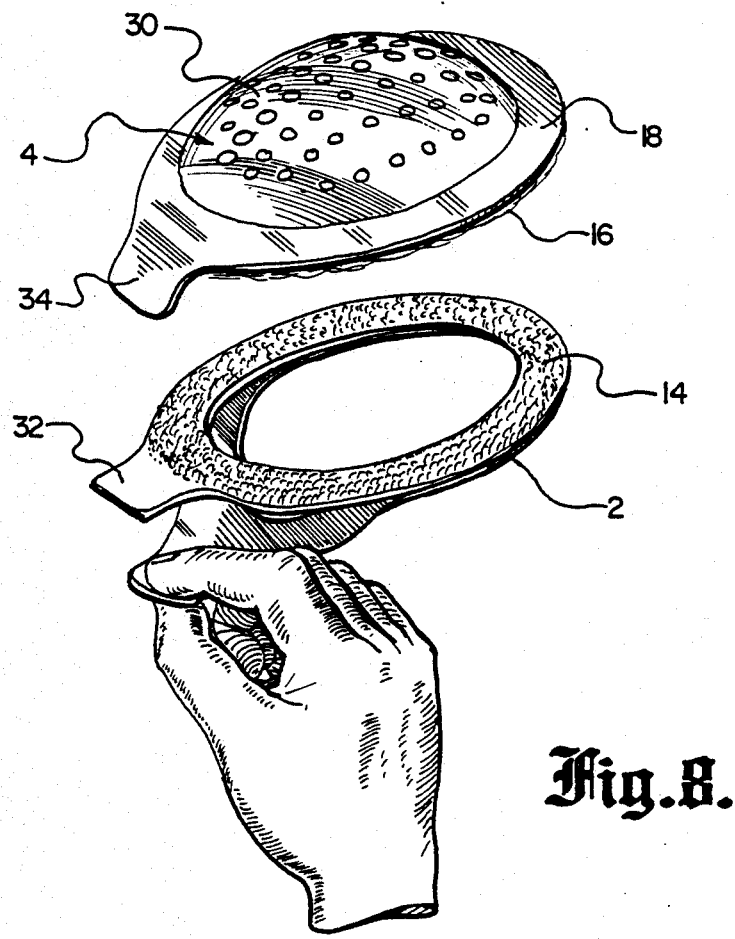
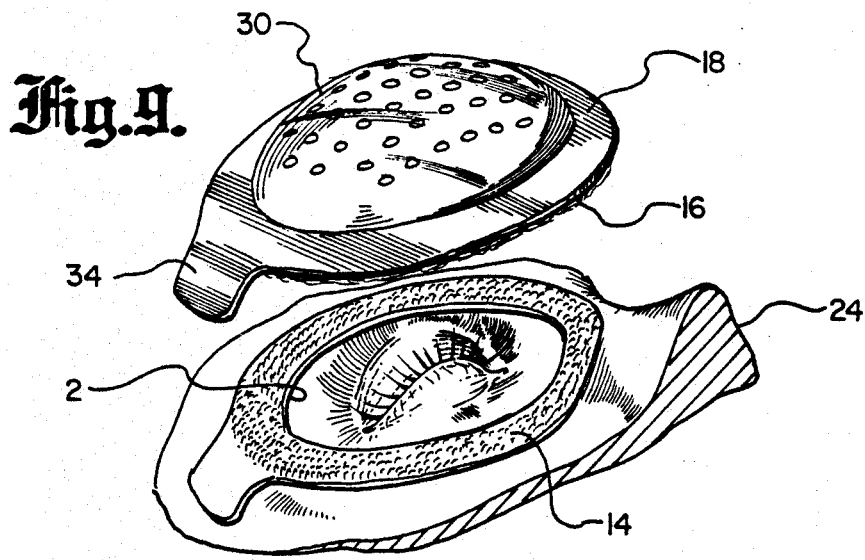

PROTECTIVE DEVICE

FIELD OF THE INVENTION

The invention relates to a device for binding protective coverings onto patients. The protective coverings may serve as bandages, moisture chambers, eye patches and the like. More particularly, the invention relates to adhesive bases which are adhesively attachable to a patient's skin and to which protective coverings can be easily coupled and repeatedly decoupled and recoupled without detaching the adhesive base from the patient's skin, so as to provide repeated ready access to the protected area without disturbing the attachment to the patient's skin.

BACKGROUND OF THE INVENTION

Protective coverings, including bandages and eye patches, are widely employed in the medical arts for providing protection for various surface injuries, wounds, lesions, pathologies, and other disease conditions. Such protective coverings are employed for variety of purposes, e.g. the positioning and retention of dressings, the protection of applied medications, the control of sepsis, the provision or removal of moisture, the application of pressure, the protection from physical contact, the blocking of light, etc. In many of these applications, repeated access to the protected area is required for periodic inspections or irrigations of the protected area, for applying fresh medications and fresh dressings, for the addition of moisture, etc. Easy access to the protected area is desirable in such cases. Preferably, such a protective covering should be easily applied and easily and repeatably detached and re-attached without injuring the adjoining tissues which underlie the support for such protective covering.

Non-adhesive bandages and eye patches constitute one class of prior art device which can provide repeated access to the protected area without damaging the tissues which underlie and support such protective coverings. A typical non-adhesive bandage or eye patch includes a band or strap which wraps around a body part so as to position and secure the protective covering over the protected area. Examples of prior art non-adhesive eye patches are provided in U.S. Pat. Nos. 377,835 (Lyman & Johnson), 3,339,206 (Daley), and 4,473,370 (Weiss). Each of the above patents discloses an eye patch which is positioned by a strap which wraps around the patient's head and which secures the eye patch over the patient's eye. Access to the eye is provided by disengaging the strap and removing the eye patch. Similar non-adhesive bandages are also employed in the prior art for securing protective coverings at other anatomic sites. However, if the patient is physically active, non-adhesive devices can sometimes slip so as to dislocate the protective covering and expose the protected area. Additionally, the inaccessibility or highly flexural nature of various anatomic sites can render the employment of non-adhesive devices impractical. Also, even at anatomic sites which are accessible and minimally flexural, the presence of adjacent pathologies may complicate the attachment of non-adhesive protecive covers. Finally, as compared to the attachment of adhesively bound protective coverings, the attachment of non-adhesive devices is often slower, more cumbersome, and therefore less advantageous. Under such circumstances, the clinician may consider employing an adhesively bound protective covering.

Examples of prior art for adhesively bound protective coverings are disclosed in U.S. Pat. Nos. 3,068,863 (Bowman), 3,092,103 (Mower), and 3,952,735 (Wirtschafter et al.). Each of the above patents discloses an adhesive eye patch device having a protective portion and an adhesive portion. The protective portion is centered within the adhesive portion. The protective portion is positioned over the area to be protected while the adhesive portion attaches securely to the patient's skin around the perimeter of the protected area. However, to provide repeated access to the protected area, it is necessary to repeatedly peel off the adhesive portion from the patient's skin. Repeatedly detaching and reattaching the adhesive portion to and from the patient's skin can be painful and damaging to the tissues which underlie and support the adhesive portion. The tissue damage caused by repeatedly detaching the adhesive portion can be lessened by employing adhesives which form a weaker bond between the adhesive portion and the patient's skin. However, employing weakly bonding adhesives reduces the security with which the protective portion is positioned over the protected area and increases the possibility that the device will be accidently dislodged, so as to expose the protected area.

Another related device, an eye lid coupler (e.g. the Donaldson Natural Eyepatch, distributed by Keeler Instruments, Inc., Broomall, PA), serves to couple opposing eye lids so as to secure the eye lids in a closed position. The eye lid coupler has two parts, viz. a first Velcro (TM) pad adhesively attached to one eye lid and second Velcro (TM) pad extending from a strap which is adhesively attached to the opposing eye lid. One of the Velcro (TM) pads is composed of Velcro (TM) hooks and the other is composed of Velcro (TM) fuzz. To secure the opposing eye lids in a closed position, the first Velcro (TM) pad is coupled to the second Velcro (TM) pad. Since the eye lid coupler is adhesively anchored to the opposing eye lids, the eye lids will be secured in a closed position when the device is coupled to itself. To release the eye lids, the two Velcro (TM) pads are uncoupled from one another. The eye lid coupler may be repeatedly secured and released so as to provide easy access to the patient's eye. This easy access to the patient's eye is achieved without detaching the adhesive bonds between the device and the respective eye lids. The eye lid coupler is employed for securing the eye lids in a closed position. The secured eye lids protect the eye as a natural protective covering.

Another related device is the Photo-Mask (Rocky Mountain Medical Corpoartion, Englewood, Colorado). The Photo-Mask is employed for blocking ultra violet light from the eyes of infants receiving photo therapy. The Photo-Mask includes an opaque mask which spans across the infant's eyes. Velcro (TM) tabs extend from both ends of the mask. This mask is secured to the infant by attachment of the Velcro (TM) tabs to a pair of Velcro (TM) base pads, which, in turn, are adhesively attached to the lower portion of the infant's temples. The infant can be repeatedly unmasked and remasked by detaching and re-attaching the Velcro (TM) tabs to and from the Velcro (TM) base pads. The Velcro (TM) base pieces of the Photo-Mask do not encircle or surround the infant's eye.

What is desired is a protective device having an adhesive base which adhesively attaches to the patient's skin, which serves to secure protective coverings such as bandages, moisture chambers, eye patches, and the like, and which can be easily and repeatedly coupled and uncoupled to and from the protective coverings so as to provide easy repeated access to the protected area with minimal pain or injury to the underlying tissues.

SUMMARY OF THE INVENTION

The invention includes an adhesive base which is adhesively attachable to a patient's skin and to which various protective coverings may be coupled and repeatedly decoupled and recoupled. The invention also includes the combination of the adhesive base and the various protective coverings. Finally, the invention includes methods for employing such adhesive bases and protective coverings.

The adhesive base is composed of a section of sheet material, e.g. cloth fabric, coated paper, sheet plastics having compositions such as acetate, vinyl, and polyethylene, or other sheet material of the type used in the prior art for making adhesive bandages. The bottom portion of the adhesive base is coated with an adhesive layer of the type used in the prior art for adhesively attaching the above sheet material to the skin of a patient. As in the adhesive bandages from the prior art, the composition of the sheet material and the adhesive of the adhesive base are chosen so as to minimize the maceration of the patient's skin caused by prolonged contact with the adhesive base and so as to minimize the potential for allergic reaction and/or inflamation of the skin.

The top portion of the adhesive base may include a means for securing the various protective covers thereto. The securing means may include any of various pressure sensitive adhesives and/or Velcro (TM). Velcro (TM) is a fastening material having a first surface composed of small hooks and an opposing surface composed of fuzz material which adheres to the first surface when ensnared by the small hooks. For purposes of the protective device, Velcro (TM) may be considered a functional equivalent to the pressure sensitive adhesives. The securing means is designed to allow the protective covering to couple and repeatedly decouple and recouple to the adhesive base without causing the adhesive base to become detached from the patient's skin. When attached to the patient, the adhesive base surrounds a protected area, e.g., the patient's injury, wound, lesion, etc. The adhesive base may consist of a single piece which forms a closed loop around the protected area, such as an oval shaped piece, or may include a plurality of pieces assembled to surround the protected area.

After the adhesive base is attached to the patient's skin, the protective covering may be coupled by its perimeter to the adhesive base. When thus secured to the adhesive base, the protective covering bridges across a protected area, i.e. the injury, wound, lesion, etc., so as to provide protection to such protected area. The adhesive base and the perimeter of the protective covering are secured to one another by means of either opposing Velcro (TM) pads or pressure sensitive adhesive. To decouple the protective covering from the adhesive base, the user merely peels the protective covering from the adhesive base. The adhesive base and the protective covering may include finger tabs for facilitating this decoupling process in a way which helps to prevent any unintended detachment of the adhesive base from the patient's skin. Likewise, the adhesive base and the protective covering may be attached on one side, such that this side of the attachment behaves like a hinge as the protective covering is repeatedly coupled and decoupled from the adhesive base. The process of decoupling and recoupling the protective covering is repeatable.

A wide variety of protective coverings may be employed with this invention. Examples include most types of prior art eye patches, e.g. rigid eye patches composed of metal, hard plastic, etc.; vented and unvented eye patches; transparent and opaque eye patches; eye patches composed of cellophane, paper, Saran (TM), various sheet plastics, or fabric; eye patches which compress a dressing against the eye and eye patches which protect the eye from physical contact; etc. Further examples of protective coverings include the protective portions of most types of prior art bandages e.g. bandages for binding a dressing; bandages for compressing a protected area; unvented moisture chambers; bandages for controlling sepsis; etc. However, to be employed with this invention, the protective covering must be capable of coupling and repeatedly decoupling and recoupling with an adhesive base without causing the adhesive base to become detached from the patient's skin.

The adhesive base is novel because it is the first such device to adhesively attach to the patient's skin, to couple to a protective covering, and to provide easy and repeated atraumatic access to a protected area without repeatedly detaching from the patient's skin.

FIG.'s 8, 9, 10 and 11 illustrate the sequence for a method for employing a protective device for compressing a gause dressing onto a patient's eye.

FIG. 8 illustrates a perspective view of the process of removing the peel away layer from the bottom side of the adhesive base for exposing a layer of pressure sensitive adhesive.

FIG. 9 illustrates a perspective view of the attachment of the adhesive base of the device of FIG. 8 to the patient's skin and the alignment of the perimeter of the protective covering with the Velcro (TM) lining atop the adhesive base.

Figure 10:
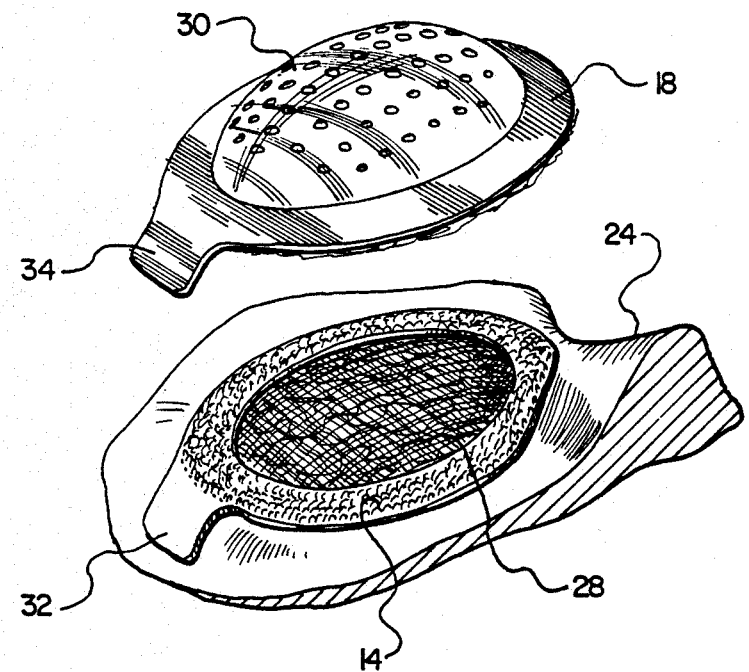

FIG. 10 illustrates a perspective view of the device of FIG. 9 with a gauze dressing covering the eye.

Figure 11:
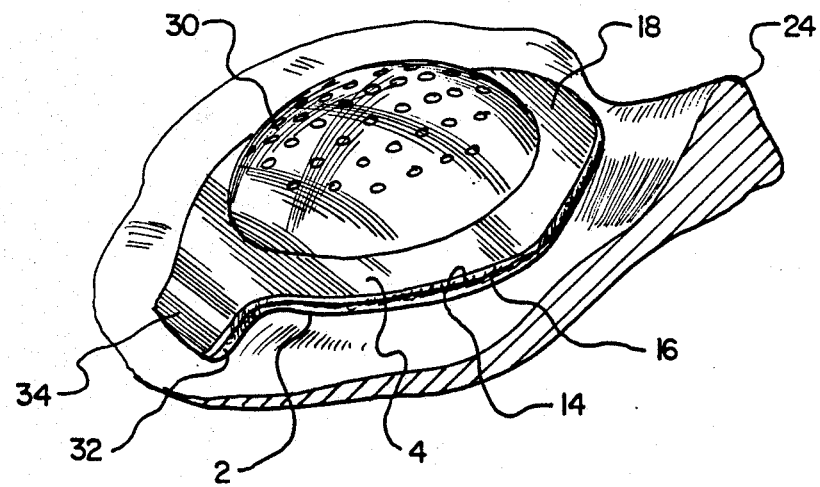

FIG. 11 illustrates a perspective view of the device of FIG. 10 with the protective covering coupled to the adhesive base, so as to compress the gauze dressing against the patient's eye.

DETAILED DESCRIPTION

Figure 3:
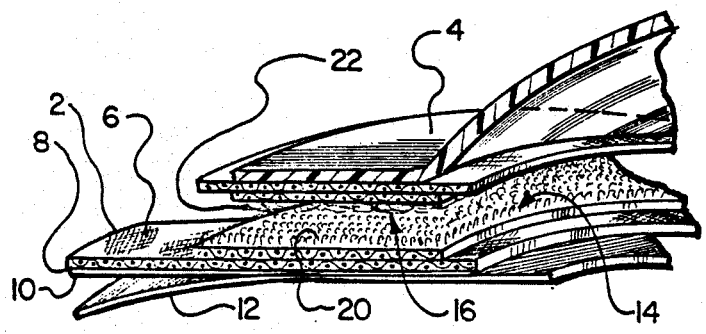
FIG. 3 is an enlarged sectional view of the device of FIG. 1, prior to its attachment to the patient, illustrating a peel away layer protecting the pressure sensitive adhesive on the bottom side of the adhesive base sheet; illustrating a section of the protective covering; and illustrating the Velcro (TM) hooks on the adhesive base and the Velcro (TM) fuzz on the protective covering for coupling the adhesive base to the protective covering.

A protective device which serves as a reattachable eye patch is illustrated in FIG.'s 1, 2, and 3. The reattachable eye patch includes two separate parts, viz. an adhesive base (2) and a protective covering (4). The adhesive base (2) is made from a base sheet material (6) having a composition similar or identical to the breathable surgical tape described in U.S. Pat. No. 3,121,021 (Copeland), incorporated herein. The bottom side (8) of the base sheet material (6) is coated with an adhesive coating (10). Pressure sensitive adhesives, of the type described in Copeland, are a preferred composition for the coating (10). Additionally, a peel away layer (12) of coated paper may be employed to protect the pressure sensitive adhesive during storage. The peel away layer is illustrated in FIG. 3. The peel away layer (12) is removed so as to expose the pressure sensitive adhesive (10) directly prior to the application of the protective device. The adhesive base (2) also includes a Velcro (TM) pad or lining (14) which can couple to an opposing Velcro (TM) pad or lining (16) along the perimeter (18) of the protective covering (4). The Velcro (TM) lining (14) serves to secure the protective covering (4) to the adhesive base (2). The opposing Velcro (TM) pads or lining (14 & 16) include Velcro (TM) hooks (20) and Velcro (TM) fuzz (22).

Figure 1:
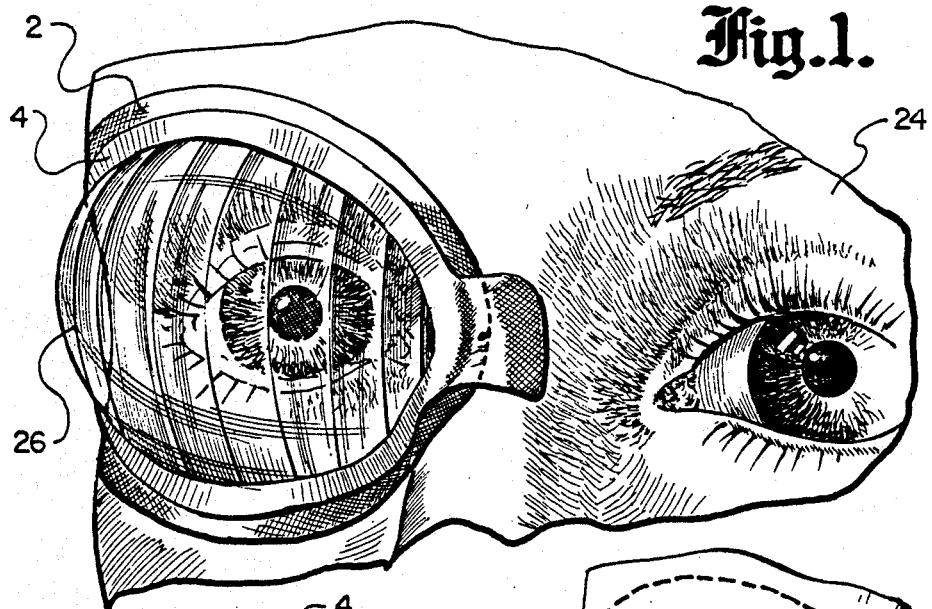
FIG. 1 is a perspective view of a transparent eye patch serving as a protective covering coupled to an adhesive base attached to the skin of a patient. The protective covering illustrated in FIG. 1 includes finger tabs.
Figure 2:
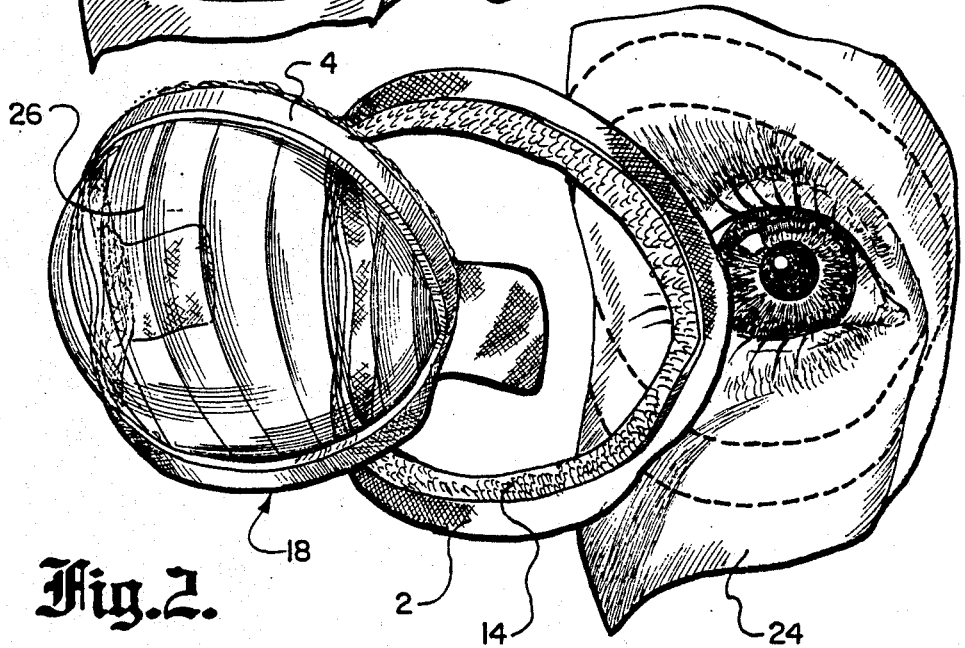
FIG. 2 is an exploded view of the device of FIG. 1, illustrating the Velcro (TM) coupling between the adhesive base and the protective covering and illustrating the adhesive attachment between the adhesive base and the patient's skin surrounding the eye socket.

FIG. 2 illustrates the application of the reattachable eye patch to the patient (24). After the peel away layer (12) is removed, the adhesive base (2) is attached to the patient (24), so as to surround the patient's eye socket. The protective covering (4) is then coupled by means of the Velcro (TM) pads or lining (14 & 16) to the adhesive base (2).

A large variety of protective coverings (4) may be employed with the protective device. FIG.'s 1, 2 & 3 illustrate a transparent eye patch which serves as a moisture chamber. In this embodiment, the protective covering (4) is composed of a single piece having a transparent semi-flexible plastic composition (26) (e.g., polyethylene sheet, Saran (TM), etc.) which spans over the eye socket. The protective covering (4) is sufficiently flexible to allow it to comform to the shape of the patent's eye socket and sufficiently rigid to maintain an arched shape. The protective covering (4) is secured to the adhesive base (2) by means of the Velcro (TM) pads or lining (14 & 16) and thereby isolates the eye so as to minimize evaporative losses. The protective covering (4) is transparent so as to allow a clinician to see eye tissue underneath the covering (4) and to monitor the moisture level within the protected area. If the protected area becomes dry, moisture may be added by temporarily decoupling the protective covering (4) from the adhesive base (2). The moisture chamber is then re-established by recoupling the protective covering (4) to the adhesive base (2).

FIG.'s 8, 9, 10, and 11 illustrate an alternative embodiment of the protective device, viz. a reattachable eye patch for compressing a dressing (28) against the eye. This embodiment includes a perforated metallic protective covering (30) having a Velcro (TM) lining or a series of Velcro (TM) pads around its perimeter (18). This embodiment serves to compress a gauze dressing (28) against the eye. In this particular case, the Velcro (TM) serves not only to secure the attachment of the protective covering (30), but also serves to compress the gauze dressing (28) onto the eye. If the gauze dressing (28) needs periodic changing, access is achieved by temporarily decoupling the protective covering (30) from the adhesive base (2).

The reattachable eye patch of FIG.'s 8, 9, 10, and 11 also includes optional tabs (32 & 34) attached to both the adhesive base (2) and to the corresponding protective covering (4). These tabs (32 & 34) facilitate the process of coupling and repeatedly decoupling and recoupling the protective covering (4) to and from the adhesive base (2) without detaching the adhesive base (2) from the patient's skin. To decouple the protective covering (4) from the adhesive base (2), the tab (32) attached to the adhesive base (2) is held down against the patient's skin (24) while the tab (34) attached to the protective cover is pulled upward so as to peel the protective cover away from its adhesive base (2). Employing such tabs (32 & 34) to initiate the decoupling process reduces the tendency to inadvertantly detach the adhesive base (2) from the patient's skin (24) while decoupling the protective covering (4). Employment of such tabs (34) on the adhesive base (2) can also facilitate the intentional removal of the adhesive base (2) from the patient's skin when it is to be discarded.

Figure 5:
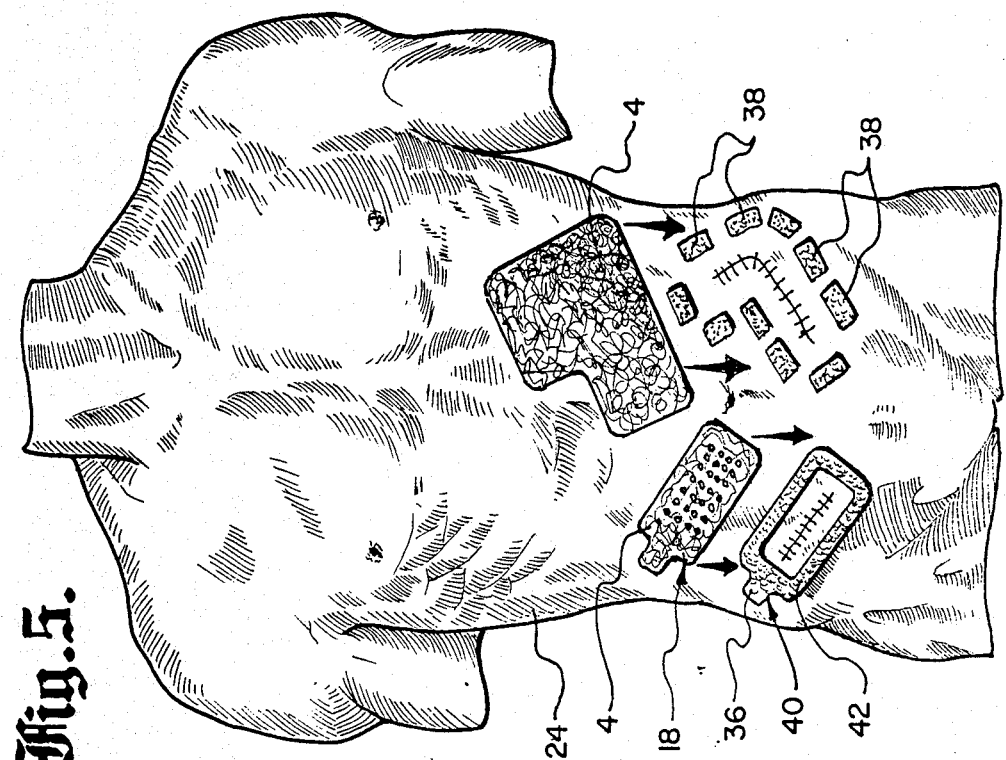
FIG. 5 is a perspective view of the process of attaching two types of reattachable bandages to a patient, viz. a first reattachable bandage using the felt protective covering shown in FIG. 4 for attachment to the Velcro (TM) pads of the multiple adhesive bases encircling an "L" shaped lesion and a second reattachable bandage having a protective covering with a standard rectangular shape and connected to its adhesive base by means of pressure sensitive adhesive.

FIG. 5 illustrates two further embodiments of the protective device, viz. a re-attachable bandage having a unitary adhesive base (36) and a re-attachable bandage having an adhesive base composed of multiple pieces (38). Both embodiments are particularly adaptable for protecting lesions at diverse body sites. FIG. 5 illustrates the protection of abdominal lesions.

A variety of materials can be employed to fabricate re-attachable bandage type protective coverings (4) attachable to unitary adhesive bases (36). Employable compositions for the protective covering (4) include many types of fabrics and plastic sheet materials employed in the prior art for making adhesive bandages, e.g. Gore-Tex (TM). Additional compositions include metal, hard plastic, flexible plastic, cellophane, etc. The preferred composition for the protective covering (4) will depend upon the particular application.

Figure 4:
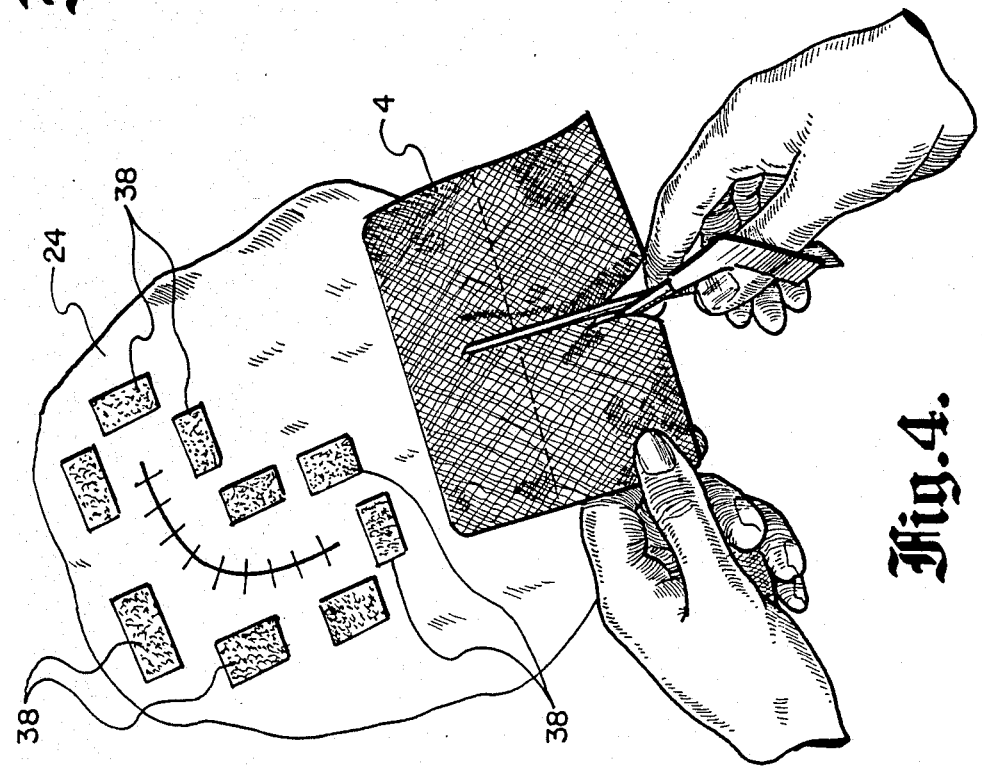
FIG. 4 is a perspective view of stock felt sheet material being cut into a shape which is employable for the felt protective covering illustrated in FIG. 5.
Figure 6:
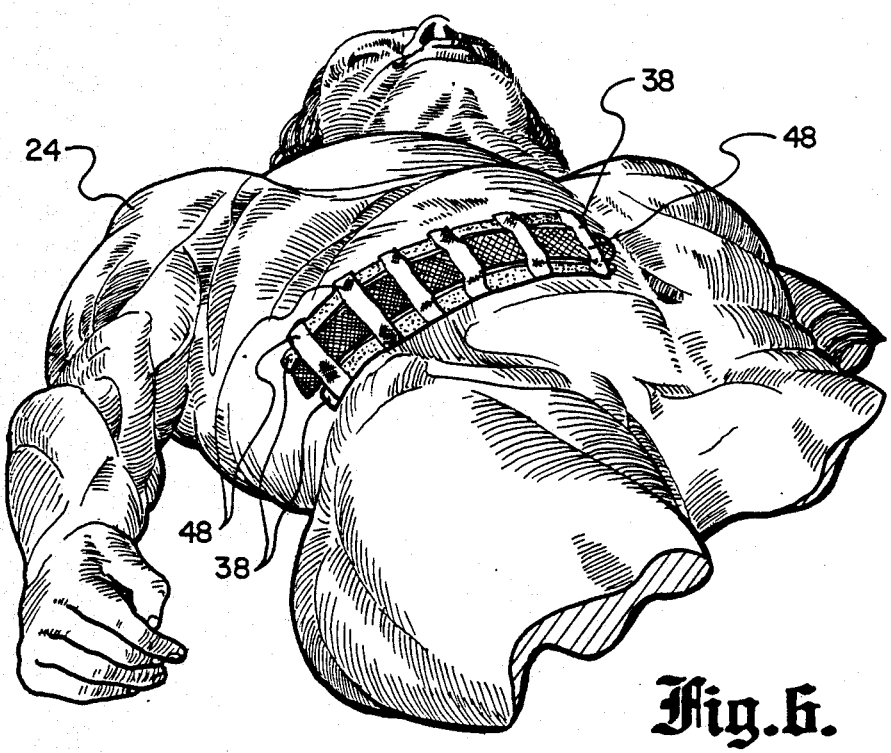
FIG. 6 illustrates parallel adhesive bases employed with multiple protective coverings for binding a dressing.
Figure 7:
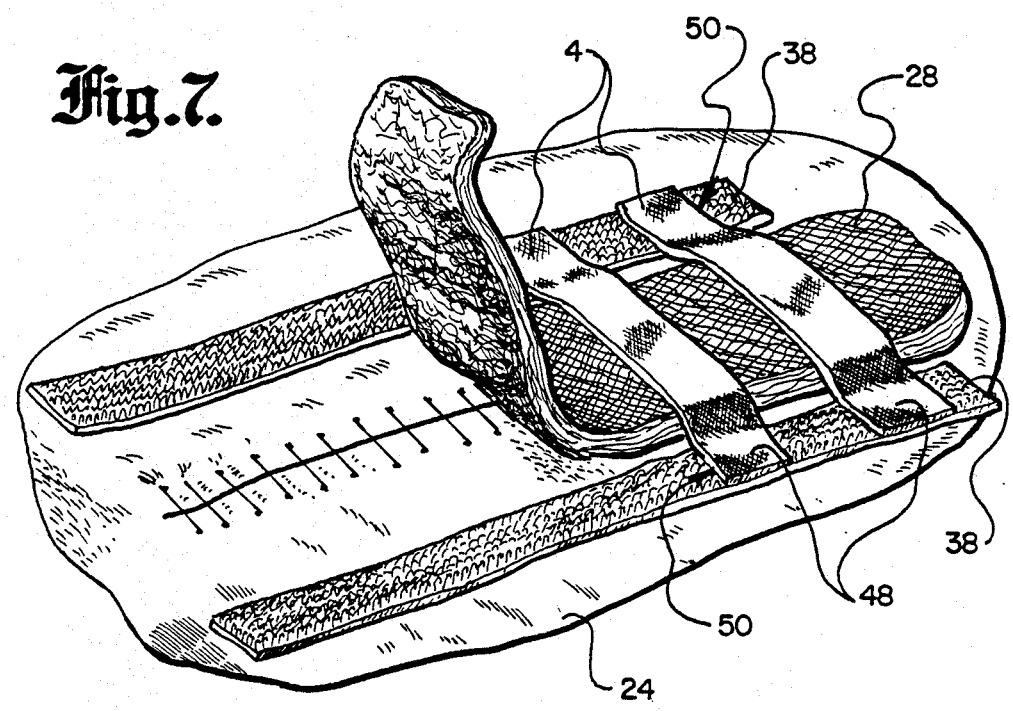
FIG. 7 is an enlarged, partially disassembled, view of the protective device of FIG. 6, additionally illustrating a partially exposed portion of the protected area, including a sutured incision.

The unitary adhesive base (36) illustrated in FIG. 5 is secured to its protective covering (4) by means of a layer of pressure sensitive adhesive (40) coated onto the upper side (42) of the unitary base (36). In turn, the protective covering (4) includes a perimeter (18) having an outer geometry which is superimposable onto the unitary base (36) and having a composition which is attachable to the layer of pressure sensitive adhesive (40). The perimeter (18) of the protective covering (4)

may passively attach to the unitary adhesive base (36) or may include a second layer of pressure sensitive adhesive Alternatively, the top side of the unitary adhesive base (36) may lack adhesive and may attach passively to a layer of pressure sensitive adhesive coated onto the perimeter of the protective covering (4). The securing means for such unitary adhesive bases (36) may also include Velcro (TM) pads or liners FIG.'s 4 & 5 also illustrate a protective bandage having an adhesive base (38) composed of multiple pieces. In this embodiment, the protective covering (4) is composed of a felt like material and is secured to the adhesive base (38) by means of Velcro (TM) pads or linings. Adhesive bases (38) having multiple pieces can be employed to protect irregularly shaped lesions. Such protective bandages can be individually taylored for each lesion. Firstly, a supply strip of adhesive base (38) material is cut into sections which are then assembled and attached to the patient (24) so as to surround the lesion by forming a substantially closed loop. Then, the protective covering (4) is cut from a supply sheet of material having a compostion such as felt which can adhere to the Velcro (TM) pad or lining (14), as illustrated in FIG. 4. The perimeter of the protective covering (4) is taylored to the shape of the assembled adhesive base (38) strips. If a dressing is to be used, the dressing is first applied to the lesion and the felt protective covering (4) is then placed atop the assembled adhesive base (38) strips and attached thereto. This particular embodiment of the reattachable bandage is highly adaptable to many types of applications.

FIG.'s 6 & 7 illustrate a further embodiment of the protective device, viz. a reattachable bandage having multiple protective coverings (4). The protective coverings (4) are composed of several strips or cords (48) which span across the protected area and attach to the opposing adhesive bases (38) which bracket the wound. The strips (48) may have a cloth, plastic, paper, leather, metal, or rubber composition. The end portions (50) of these strips (48) include a means for coupling to the adhesive base (38), e.g. Velcro (TM) pads. The reattachable bandage having multiple protective coverings (4) is particularly useful for protecting areas which are highly flexural and for which the patient (24) needs the greatest possible freedom of movement. The dressing (28), illustrated in FIG.'s 6 & 7, also serves as part of the protective covering (4); in turn, the straps serve to retain the dressing (28) in its position atop the protected area.

The ability to decouple the protective covering (4) from the adhesive base (2) without detaching the adhesive base (2) from the patient's skin (24) is an essential aspect of all embodiments of the protective device. Several means may be employed to impart this trait. Firstly, this trait can be enhanced by employing the tabs (32 & 34) illustrated in FIG.'s 8, 9, 10 and 11. Secondly, this trait will be enhanced if the bond strength between the adhesive base (2) and the patient's skin (24) exceeds the bond strength between the adhesive base (2) and the protective covering (4). Bond strengths may be increased by employing adhesives or Velcro (TM) which form tighter bonds with their respective substrates. Bond strengths may also be increased or decreased by increasing or decreasing the surface area of the particular adhesive layer or Velcro (TM) pad which engages to its respective substrate. The bond strength of the securing means between the adhesive base (2) and the protective cover can be decreased by employing a pressure sensitive adhesive on only one surface instead of both.

What is claimed is:

1. A protective device adhesively bindable to the skin of a patient for protectively enclosing a wound, the protective device comprising:
   an adhesive base having an upper surface and a lower surface, the lower surface being coated with an adhesive for adhesively binding said adhesive base to the skin of the patient, said adhesive base forming a substantially closed loop for encircling the wound,
   a protective covering for spanning over the wound and protectively enclosing the wound, said protective covering including a perimeter, and
   a means for securing said protective covering to said adhesive base, said securing means lying between the upper surface of said adhesive base and the perimeter of said protective covering, said securing means being of the type which can be repeatedly re-used and which enables said protective covering to be decoupled from said adhesive base without unbinding the adhesive base from the skin of the patient.

2. A protective device as described in claim 1 wherein:
   said securing means being affixed to the upper surface of said adhesive base.

3. A protective device as described in claim 1 wherein:
   said securing means being afixed to the perimeter of said protective covering.

4. A protective device as described in claim 1 wherein:
   said securing means including a first part and a second part, the first part being afixed to the upper surface of said adhesive base and the second part being afixed to the perimeter of said protective covering.

5. A protective device as decribed in claim 1 wherein:
   said protective covering including a tab for decoupling said protective covering from said adhesive base.

6. A protective device as described in claim 1 wherein:
   said protective covering including a tab for decoupling said protective covering from said adhesive base and
   said adhesive base including a finger tab.

7. A protective device as described in claim 1 wherein said adhesive base and the perimeter of said protective covering being integrally attached at one point like a hinge.

8. A protective device as described in claim 1 for protectively enclosing an eye socket wherein:
   said adhesive base having a shape for encircling the eye socket and
   said protective covering having a shaped adapted for protectively covering the eye socket, for securing to said adhesive base and for serving as an eye patch.

9. A protective device adhesively bound to the skin of a patient for protecting a wound, the protective device comprising:
   two or more straps for spanning over the wound,
   two or more adhesive bases,
   means for securing said straps to said adhesive bases, and a dressing secured by two or more of said straps and positioned between said straps and the wound, each of said adhesive bases having an upper surface and a lower surface, the lower surface being coated with an adhesive for adhesively binding said adhesive base to the skin of the patient, the upper surface having said securing means afixed thereto for securing said straps to said adhesive bases, two or more of said adhesive bases being arrayed about the wound for supporting said straps across the wound, said securing means being of the type which can be repeatedly re-used and which enables said protective covering to be coupled from said adhesive base without unbinding the adhesive base from the skin of the patient.

10. A method for protectively enclosing a patient's wound comprising the following steps:

encircling the wound by adhesively binding an adhesive base to the skin of the patient surrounding the wound and covering the wound by coupling a protective covering to the adhesive base, the protective covering being coupled to the adhesive base by means of a re-useable securing means lying between the protective covering and the adhesive base.

11. A method for protectively enclosing a patient's wound comprising the following steps:

bracketing the wound by adhesively binding a pair of adhesive bases to the skin of the patient on opposite sides of the wound, covering the wound with a dressing, and securing the dressing by means of two or more strap, the straps being coupled to the adhesive bases by means of a re-useable securing means lying between the straps and the adhesive base.

* * * * *